US00PP09748P

United States Patent [19]

Dümmen

[11] Patent Number: Plant 9,748

[45] Date of Patent: Dec. 10, 1996

[54] GERANIUM PLANT NAMED 'HWD VIOLETTA'

[75] Inventor: Günter Dümmen, Rheinberg-Eversael, Germany

[73] Assignee: Dummen Jungpflanzenkulturen, Rheinberg-Eversael, Germany

[21] Appl. No.: 521,603

[22] Filed: Aug. 30, 1995

[51] Int. Cl.[6] ..... A01H 5/00

[52] U.S. Cl. ..... Plt./87.12

[58] Field of Search ..... Plt./87.12

*Primary Examiner*—James R. Feyrer

*Attorney, Agent, or Firm*—Proprietary Rights International

[57] ABSTRACT

A new and distinct cultivar of geranium plant named HWD Violetta, characterized by its semi-double rubine red flowers; large umbels; large flowers; medium plant habit; and zonation pattern on foliage.

1 Drawing Sheet

The present invention relates to a new and distinct cultivar of geranium plant, botanically known as *Pelargonium×hortorum,* known as the variety Duevio, and hereinafter referred to by the cultivar name HWD Violetta.

The new cultivar is a product of a planned breeding program conducted by the inventor in Rheinberg, Germany. The objective of the breeding program was to develop a new geranium with a unique purple red flower color.

The new cultivar originated from a cross made by the inventor of the patented cultivar Fisglo (U.S. Plant Pat. No. 7,394) as the male or pollen parent with the proprietary selection 86-12-2 as the female or seed parent.

The cultivar HWD Violetta was discovered and selected by the inventor as a flowering plant within the progeny of the stated cross in a controlled environment in Rheinberg, Germany. Asexual reproduction of the new cultivar by terminal cuttings taken at Rheinberg, Germany, has shown that the unique features of this new geranium are stabilized and reproduced true to type in successive generations of asexual reproduction.

The following traits have been repeatedly observed and are determined to be the unique characteristics of HWD Violetta. These characteristics in combination distinguish HWD Violetta as a new and distinct cultivar:

1. Semi-double rubine red flowers.
2. Large umbels.
3. Large flowers.
4. Medium plant habit.
5. Zonation pattern on foliage.

In comparison to the parent cultivar Fisglo, plants of the new geranium have rubine red (not orange red) petal color, large umbels and larger flowers. In comparision to the parent proprietary selection 86-12-2, plants of the new geranium have rubine red (not orange red) petal color, smaller plant size, and zonation pattern on foliage.

The new geranium is similar in petal color to the patented cultivar Designer Rose (U.S. Plant Pat. No. 8,524) and the cultivars HWD Fuega and HWD Sorpresa (disclosed in the inventor's pending applications). In compaision to the cultivar Designer Rose, plants of the new geranium have larger umbels, and zonation pattern on the foliage. In comparison to the cultivars HWD Fuega and HWD Sorpresa, plants of the new geranium have fewer lateral branches, larger leaves, lighter leaf color, zonation pattern on the foliage, smaller umbels, smaller flowers, and flower color is more purple. Plants of the new geranium are larger than plants of the cultivar HWD Fuega, but more compact than plants of the cultivar HWD Sorpresa.

The accompanying colored photograph illustrates the overall appearance of the new cultivar, showing the colors as true as it is reasonably possible to obtain in colored reproductions of this type. Flower color appears more red than the actual flower color due to light reflectance. The photograph comprises a top perspective view of a typical potted plant of HWD Violetta with one plant in a 10-cm container.

The cultivar HWD Violetta has not been observed under all possible environmental conditions. The phenotype may vary somewhat with variations in environment such as temperature and light intensity, without, however, any variance in genotype. The following observations, measurements and comparisons describe plants grown in Rheinberg, Germany, under commercial practice in a glass-covered greenhouse with day temperatures of 24° C. and night temperatures of 18° to 20° C. and light levels of 45,000 to 60,000 lux. Plants were grown in 10-cm pots with one plant per pot.

In the following description, color references are made to The Royal Horticultural Society Colour Chart except where general terms of ordinary dictionary significance are used.

Classification:

*Botanical.*—*Pelargonium×hortorum.*

*Commercial.*—Zonal geranium.

*Cultivar.*—'HWD Violetta'.

Parentage:

*Male parent.*—Cultivar Fisglo (U.S. Plant Pat. No. 7,394).

*Female parent.*—Proprietary selection 86-12-2.

Propagation:

*Type cutting.*—Terminal cuttings.

*Time to initiate roots.*—Summer: 27° C., 21 days; winter: 20° C., 28 days.

Plant Description

General appearance: Rounded; medium plant size; upright; freely branching.

Foliage description:

*Arrangement.*—Generally alternate.

*Shape.*—Orbicular with rounded tip and cordate base.

*Size.*—Length: 7 to 8 cm. Width: 8 to 9 cm.

*Texture.*—Velvety; pubescent on upper and under surfaces.

*Margin.*—Crenate.

*Color.*—Young foliage, upper surface: 146A. Young foliage, under surface: 146A. Mature foliage, upper surface: 146A. Mature foliage, under surface: 146A. Zone, upper surface: 147A. Zone, under surface: None. Veins, upper surface: 146C. Veins, under surface: 146C.

*Zonation.*—Width of zone: 2 cm. Location of zone: 0.5 to 1 cm from margin and 2.3 cm from petiole.
*Venation pattern.*—Palmate.
*Petiole.*—Length: 5 to 6 cm. Diameter: 2 to 2.5 mm. Color: 146C.

Stem description:
*Internode length.*—0.7 to 1 cm.
*Lateral branch number.*—5.
*Lateral branch length.*—7 to 10 cm.

Flowering Description

Flowering habit: Freely flowering. Flowers aranged in umbels.
Natural flowering season: Year-round.
Flowers borne: Flower buds develop in apical leaf axils. Umbels are displayed above the foliage.
Quantity of inflorescences: Usually 6 to 7 open umbels and at least 4 developing umbels per plant at one time.

Umbels:
*Form.*—Rounded.
*Diameter.*—11 cm.
*Depth (height).*—6 cm.

Flowers
*Form.*—Semi-double.
*Shape.*—Rounded.
*Quantity of flowers per umbel.*—22.
*Diameter.*—4.5 to 5 cm.
*Depth (height).*—1.5 cm.

Petals:
*Shape.*—Obovate with rounded tip.
*Arrangement.*—Rosette, overlapping.
*Quantity.*—5 to 6.
*Aspect.*—Flat.
*Size.*—Length: 2.5 cm. Width: 2 to 2.3 cm.
*Texture.*—Satiny, smooth.
*Margin.*—Entire.
*Color.*—When opening, upper surface: 57A. When opening, under surface: 58B. Upper surface: 57A. Under surface: 58B. Fading to, upper surface: 40D. Fading to, under surface: No fading observed.

Petaloids:
*Shape.*—Irregular, generally obovate with rounded or clefted tip.
*Arrangement.*—Rosette, overlapping.
*Quantity.*—3 to 5.
*Size.*—Length: 2 cm. Width: 0.9 to 1.9 cm.
*Texture.*—Satiny, smooth.
*Margin.*—Generally entire.
*Color.*—When opening, upper surface: 57A. When opening, under surface: 58B. Upper surface: More red than 57A. Under surface: 58B. Fading to, upper surface: 40D. Fading to, under surface: No fading observed.

Peduncle (umbel stem):
*Angle.*—Erect, rigid.
*Length.*—10.5 to 15 cm.
*Pubescence.*—Very fine, sparse.
*Color.*—146B/146C.

Pedicel (individual flower stem):
*Angle.*—Erect, rigid.
*Length.*—3.2 cm.
*Pubescence.*—Very fine.
*Color.*—53A.

Flower bud:
*Shape.*—Ovoid.
*Length.*—1.5 cm.
*Diameter.*—9 mm.
*Color.*—Darker red than 45A.

Sepals:
*Arrangement.*—Rosette.
*Quantity.*—5.
*Size.*—Length: 1 to 1.2 cm. Width: 3 to 4 mm.
*Shape.*—Acuminate with apiculate tip.
*Texture.*—Velvety.
*Margin.*—Entire.
*Color.*—Upper surface: 57A at base fading to 143C at tip. Under surface: 57A at base fading to 143C at tip.

Reproductive organs:
*Androecium.*—Stamen number: 11 to 12. Anther size: 2 mm. Anther color: 53B. Pollen color: 34A.
*Gynoecium.*—Pistil number: 1. Pistil length: 1 cm. Stigma shape: Decurrent. Stigma color: 61B. Style length: 4 mm. Style color: 61B.

Ploidy level: Tetraploid.
Disease resistance: No fungal, bacterial nor viral problems observed.
Seed development: Seed production is very rarely observed.

It is claimed:

1. A new and distinct cultivar of geranium plant named HWD Violetta, as illustrated and described.

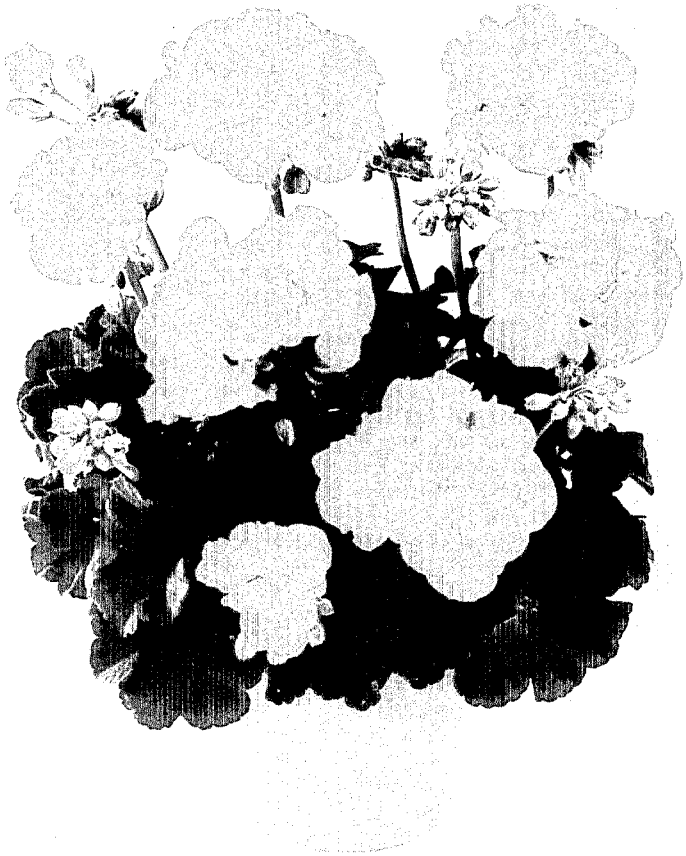

* * * * *